US008106199B2

(12) United States Patent
Jabbour et al.

(10) Patent No.: US 8,106,199 B2
(45) Date of Patent: Jan. 31, 2012

(54) ORGANOMETALLIC MATERIALS FOR OPTICAL EMISSION, OPTICAL ABSORPTION, AND DEVICES INCLUDING ORGANOMETALLIC MATERIALS

(75) Inventors: Ghassan E. Jabbour, Phoenix, AZ (US); Jian Li, Phoenix, AZ (US)

(73) Assignee: Arizona Board of Regents for and on behalf of Arizona State University, Scottsdale, AZ (US)

(*) Notice: Subject to any disclaimer, the term of this patent is extended or adjusted under 35 U.S.C. 154(b) by 573 days.

(21) Appl. No.: 12/030,798

(22) Filed: Feb. 13, 2008

(65) Prior Publication Data

US 2008/0269491 A1 Oct. 30, 2008

Related U.S. Application Data

(60) Provisional application No. 60/889,719, filed on Feb. 13, 2007.

(51) Int. Cl.
C07F 15/00 (2006.01)
H01L 51/50 (2006.01)
(52) U.S. Cl. ............... 546/10; 428/690; 313/504; 546/2
(58) Field of Classification Search .................. 546/2, 10; 428/690; 313/504
See application file for complete search history.

(56) References Cited

U.S. PATENT DOCUMENTS

| 7,026,480 B2 | 4/2006 | Che et al. |
| 7,029,766 B2 | 4/2006 | Huo et al. |
| 7,166,368 B2 | 1/2007 | Lecloux et al. |
| 7,276,617 B2 | 10/2007 | Sotoyama et al. |
| 2002/0189666 A1 | 12/2002 | Forrest et al. |
| 2006/0093854 A1 | 5/2006 | Sotoyama et al. |
| 2006/0094875 A1 | 5/2006 | Itoh et al. |
| 2007/0111025 A1 | 5/2007 | Lennartz et al. |
| 2007/0224447 A1 | 9/2007 | Sotoyama et al. |
| 2008/0067925 A1 | 3/2008 | Oshiyama et al. |

FOREIGN PATENT DOCUMENTS

| JP | 2006114889 A | 4/2006 |
| JP | 2006282965 A | 10/2006 |
| WO | WO 00/70655 | 11/2000 |
| WO | WO2004/039781 | 5/2004 |
| WO | WO2005/075600 | 8/2005 |
| WO | WO2005/103195 | 11/2005 |
| WO | WO2005/105746 A1 | 11/2005 |
| WO | WO2006/082742 A1 | 8/2006 |
| WO | WO2006/100888 | 9/2006 |
| WO | WO2009/086209 | 7/2009 |
| WO | WO2009/111299 | 9/2009 |

OTHER PUBLICATIONS

Ionkin, A.S. et al.: Synthesis and structural characterization of a series of novel polyaromatic ligands containing pyrene and related biscyclometalated iridium complexes. Organometallics, vol. 25, pp. 1461-1471, 2006.*
Adamovich, V. et al., "High efficiency single dopant white electrophosphorescent light emitting diodes", New J. Chem., 2002, 26, pp. 1171-1178.
Del Caño, Teodisio et al., "Near-infrared electroluminescence based on perylenediimide-doped tris(8-quinolinolato) aluminum," Appl. Phys. Lett. 88(7): 071117 (2006).
Forrest et al., "Measuring the Efficiency of Organic Light-Emitting Devices," Advanced Materials 15(13): 1043-1048 (2003).
Harrison et al., "Near-Infrared Electroluminescence from conjugated polymer/lanthanide porphyrin blends," Appl. Phys. Lett. 79: 3770-3772 (2001).
Kido et al., "Organo Lanthanide Metal Complexes for Electroluminescent Materials," Chem. Rev. 102(6): 2357-2368 (2002).
Lamansky et al., "Highly phosphorescent bis-cyclometalated iridium complexes: synthesis, photophysical characterization, and use in organic light emitting diodes," J. Am. Chem. Soc. 123(18): 4304-12 (2001).
Lamansky et al., "Synthesis and characterization of phosphorescent cyclometalated iridium complexes," Inorg. Chem.40(7): 1704-1711 (2001).
Li et al., "Synthesis and properties of novel poly(p-phenylenevinylene) copolymers for near-infrared emitting diodes," European Polymer Journal 41(12): 2923-2933 (Dec. 2005).
Peumans et al., "Small Molecular Weight Organic Thin-Film Photodetectors and Solar Cells," Journal of Applied Physics, vol. 93, No. 7, pp. 3693-3723 (Apr. 1, 2003).
Rand et al., "Organic Double-Heterostructure Photovoltaic Cells Employing Thick Tris(acetylacetonato)ruthenium(III) Exciton-Blocking Layers," Advanced Materials 17(22): 2714-2718 (2005).
Tang, C.W., "Two-layer organic photovoltaic cell," Appl. Phys. Lett. 48(2): 183-185 (1986).
Vanhelmont F. W. M et al., "Synthesis, crystal structure, high-resolution optical spectroscopy, and extended Huckel calculations for [Re(CO)$_4$(thpy)] (thpy-=2-(2-Thienyl)pyridinate). Comparison with related cyclometalated complexes," Inorganic Chemistry 36(24): 5512-5517 (1997). Williams et al., "Organic light-emitting diodes having exclusive near-infrared electrophosphorescence," Applied Physics Letters 89: 083506 (2006), 3 pages.
S. A. Wilson et al., "A Luminescent Platinum(II) 2,6-Bis(N-pyrazolyl)pyridine Complex", Inorg. Chem. vol. 43, pp. 2548-2555, 2004.
J. M. Longmire et al., "Synthesis and X-ray Crystal Structures of Palladium(II) and Platinum(II) Complexes of the PCP-Type Chiral Tridentate Ligand", Organometallics, vol. 17, pp. 4374-4379, 1998.
Cardenas et al., "Divergent Behavior of Palladium(II) and Platinum(II) in the Metalation of 1,2-Di(2-pyridyl) benzene," Organometallics 1999, 18, pp. 3337-3341.
Williams et al., "An Alternative Route to Highly Luminescent Platinum(II) Complexes," Inorg. Chem., 2003, 42, pp. 8609-8611.
Sanna et al., "Platinum complexes with N-N-C ligands. Synthesis, electrochemical and spectroscopic characteristics of platinum(II) and relevant electroreduced species," Inorganica Chimica Acta 305, 2000, pp. 189-205.
International Search Report and Written Opinion, PCT/US2008/087847, mailed Aug. 6, 2009, 12 pages.
International Search Report and Written Opinion, PCT/US2009/03544, mailed Oct. 19, 2009, 14 pages.

* cited by examiner

*Primary Examiner* — Charanjit Aulakh
(74) *Attorney, Agent, or Firm* — Fish & Richardson P.C.

(57) ABSTRACT

A near infrared phosphorescent organometallic complex includes a cyclometalating ligand and a transition metal. The cyclometalating ligand includes a fused aromatic ring structure with carbon atoms, and a heteronuclear aromatic ring with a nitrogen atom. The transition metal is bonded to the nitrogen atom in the heteronuclear aromatic ring and one of the carbon atoms in the fused aromatic ring structure. The heteronuclear ring can be part of the fused aromatic ring. The organometallic complex is capable of phosphorescent emission with maximum emission intensity occurring at a wavelength in a range from about 650 nm to about 2000 nm.

10 Claims, 14 Drawing Sheets

ORGANOMETALLIC MATERIALS FOR OPTICAL EMISSION, OPTICAL ABSORPTION, AND DEVICES INCLUDING ORGANOMETALLIC MATERIALS

CROSS-REFERENCE TO RELATED APPLICATIONS

This application claims the benefit under 35 U.S.C.§119 (e)(1) of U.S. provisional application 60/889,719, filed Feb. 13, 2007, which is incorporated by reference herein in its entirety.

TECHNICAL FIELD

This invention relates to organic materials, and more specifically organometallic materials that can be used in devices for the generation, absorption, and manipulation of light.

BACKGROUND

Organic materials can be used in optoelectronic applications for the processing of light, such as in electroluminescent devices (light emission) and solar cells (light absorption). Organic optoelectronic components are typically based on a layered structure of at least one light processing (or active) layer between two electrode layers. Light processing includes light emission, light absorption, modulation of light, wavelength conversion, and waveguiding. Various organic materials are optoelectronically active such that they can be used either to emit or to detect electromagnetic radiation. For example, organic optoelectronically active materials which can be used in the manufacture of Organic Light-Emitting Devices (OLEDs) include polymers and molecules in which the structure of molecular orbitals enables excitation of electrons to a higher excited state, which is thereafter discharged in the form of electromagnetic radiation. In absorbing devices, electromagnetic radiation generates an electric current in a circuit coupled to the electrodes of the device.

FIG. 1 depicts OLED 100, which includes substrate 102 with a layer of indium tin oxide as an anode 104, a layer of hole-transporting materials (HTL) 106, a layer of light processing material 108, such as emissive materials (EML) including emitter and host for an OLED, a layer of electron-transporting materials (ETL) 110, and a metal cathode layer 112. The emission color of an OLED is determined by the emission energy (optical energy gap) of the light processing material 108. Phosphorescent OLEDs (i.e., OLEDs with phosphorescent emitters) have a higher device efficiency that other OLEDs, including fluorescent OLEDs. Light emitting devices based on electrophosphorescent emitters are described in WO 00/70655 to Baldo et al., which is incorporated by reference herein.

Referring to FIG. 2, a typical organic solar cell (photovoltaic) device 200 includes substrate 202 with a layer of a transparent conductive electrode such as indium tin oxide (or other optically transparent conductive material) as an anode 204, a layer of donor-type materials 206, a layer of acceptor-type materials 208, a layer of exciton blocking materials 210, and a layer of metal cathode 212. U.S. Patent Publication No. 2002/0189666 to Forrest et al., which is incorporated by reference herein, describes examples of organic solar cells.

FIG. 3 depicts a schematic illustration of the process involved in the generation of photocurrent from incident light in a donor-acceptor (DA) heterojunction photovoltaic cell. Photon absorption occurs with an efficiency $\eta_A$ proximate the anode 204. Exciton diffusion occurs in the donor-type material 206, where the fraction of excitons reaching the DA junction is $\eta_{ED}$. A charge transfer reaction occurs proximate the acceptor-type material 208 with efficiency $\eta_{CT}$. Collection of carriers proximate the cathode 212 occurs, with an efficiency $\eta_{CC}$.

An efficient photovoltaic cell has a high photon absorption efficiency $\eta_A$, a high exciton diffusion efficiency $\eta_{ED}$, a high charge transfer efficiency $\eta_{CT}$, and a high carrier collection efficiency $\eta_{CC}$. Absorbers with high exciton diffusion length, including certain organometallic complexes with heavy metals and triplet absorbers, provide a higher device efficiency than other known absorbers.

SUMMARY

In one aspect, an organometallic complex includes a cyclometalating ligand and a transition metal. The cyclometalating ligand includes a fused aromatic ring structure with carbon atoms and a heteronuclear aromatic ring with a nitrogen atom. The transition metal is bonded to the nitrogen atom in the heteronuclear aromatic ring and to one of the carbon atoms in the fused aromatic ring structure. The organometallic complex is capable of phosphorescent emission with maximum emission intensity occurring at a wavelength in a range from about 650 nm to about 2000 nm. In some embodiments, the wavelength of the maximum emission intensity is tunable, based on the cyclometalating ligand.

In some implementations, the transition metal is chosen from the group consisting of Pt(II), Pd(II), Ir(III), and Rh(III). The organometallic complex can include at least one additional cyclometalating ligand. In some embodiments, the fused aromatic ring structure of the cyclometalating ligand includes the heteronuclear aromatic ring. The fused aromatic ring structure of the cyclometalating ligand includes at least four fused aromatic rings.

The heavy transition metal and the cyclometalating ligand advantageously provide a broad absorption spectrum and substantially exclusive near infrared emission, with essentially no emitted light in the visible region, allowing these compounds to be used as night vision display devices.

In some implementations, the cyclometalating ligand includes a pyrenyl group. For instance, the cyclometalating ligand can be pyrenyl-pyridine, 1-pyrenyl-quinolone, pyrenyl-benziso-quinolone, or 1-pyrenyl-iso-quinolone. In some implementations, the cyclometalating ligand includes a perylenyl group. In certain implementations, the cyclometalating ligand includes an aza-oligoryne group. One or more additional aromatic rings can be fused to the aza-oligoryne group to form the cyclometalating ligand.

In some implementations, the organometallic complex includes at least one ancillary ligand, and the transition metal is bonded to two atoms of the ancillary ligand. The ancillary ligand can be, for example, acetoacetonate or a 2-phenylpyridine. The 2-phenylpyridine can be fluorinated.

In another aspect of the invention, an organometallic complex has the structure

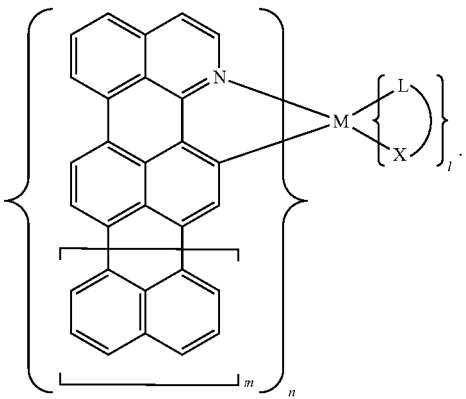

where M is a transition metal chosen from the group consisting of Pt(II), Pd(II), Ir(III), and Rh(III), L^X is an ancillary ligand, n is an integer ranging from 1 to 3, 1 is an integer ranging from 0 to 2, and m is an integer $\geq 0$. In some embodiments, one or more additional aromatic rings are fused to the azaperylene structure shown above. The organometallic complex is capable of phosphorescent emission with maximum emission intensity occurring at a wavelength in a range from about 650 nm to about 2000 nm. In some implementations, the maximum phosphorescent emission intensity occurs at a wavelength between about 650 nm and about 1000 nm.

In some implementations, light processing devices, such as OLEDs and organic solar cells, include the organometallic complexes as near infrared phosphorescent emitters and/or broadband absorbers.

In another aspect, a phosphorescent device includes a phosphorescent emitter in a host material. The phosphorescent emitter is an organometallic complex with an cyclometalating ligand having at least four fused aromatic rings. The phosphorescent emitter has an emission maximum at a wavelength between about 650 nm and about 2000 nm, and the traction of total emission attributed to near infrared is at least about 75%. In some cases, the fraction of total emission attributed to near infrared is at least about 90%.

In some implementations, the phosphorescent device is an organic light emitting device or an organic solar cell. In certain implementations, a night vision display device includes the phosphorescent device. With substantially exclusive near infrared emission, the display device is advantageously undetectable by the unaided human eye.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Organometallic complexes having strong phosphorescent emission in the near infrared region (i.e., from about 650 nm to about 2000 nm, or from about 650 nm to about 1000 nm) are described. These complexes have a transition metal bonded to one or more cyclometalating ligands. Each cyclometalating ligand includes a fused aromatic ring structure with at least four fused aromatic rings. These complexes can be used as high-efficiency, wavelength-tunable phosphorescent emitters in the fabrication of near infrared phosphorescent organic light emitting devices (PhOLEDs) and/or as absorbers in organic solar cells. The efficient, near infrared PhOLEDs can be used, for example, as night vision display devices for military, security, and bio-imaging applications.

Organometallic complexes described herein have the general structure shown below:

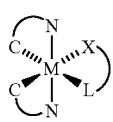

where C^N is a cyclometalating ligand, L^X is an ancillary ligand, and M is a transition metal. In some implementations, M is Pt(II), Pd(II), Ir(III), or Rh(III). C^N is a fused aromatic ring stricture including at least four fused aromatic rings. In some embodiments, C^N includes a pyrenyl group, a perylenyl group, or an analog thereof. C^N also includes a nitrogen-atom-containing heteronuclear aromatic ring. In certain embodiments, the nitrogen-atom-containing heteronuclear aromatic ring is part of the fused aromatic ring structure (i.e., the fused aromatic ring structure includes the nitrogen-atom-containing heteronuclear aromatic ring). In other embodiments, the nitrogen-atom-containing heteronuclear aromatic ring is a substituent group (or part of a substituent group) bonded to the fused aromatic ring structure.

Examples of cyclometalating ligands include pyrenyl-pyridine (pypy), 1-pyrenyl-quinoline (pyq), pyrenyl-benzisoquinolone (pybq), and 1-pyrenyl-iso-quinolone (pyiq), shown below.

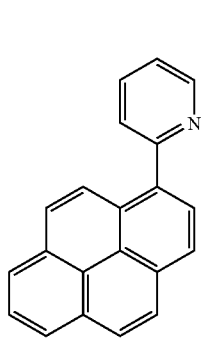
pypy

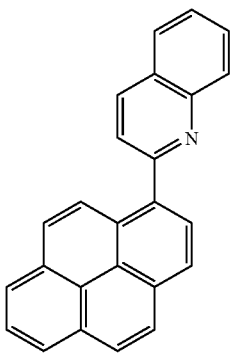
pyq

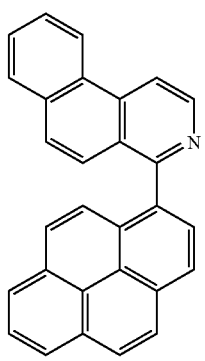
pybq

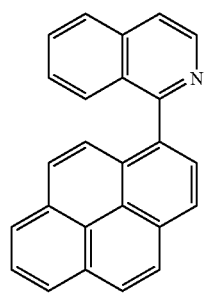
pyiq

Other cyclometalating ligands include a fused aromatic aza-oligoryne structure, as shown below, where m is an integer, and m≧0.

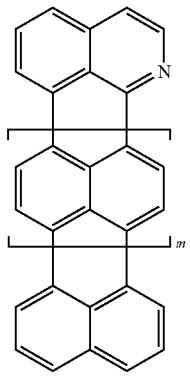

When m=0, the ligand, azaperylene (apry), has the following structure.

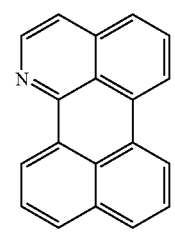

In some implementations, one or more substituents are bonded (or fused) to the aza-oligoryne structure, as shown below.

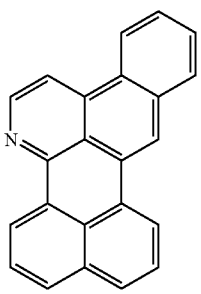 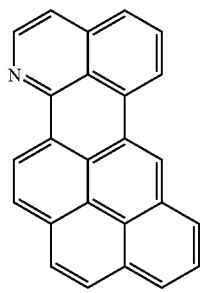

In certain embodiments, the organometallic complexes described herein include an ancillary ligand bonded to the transition metal. The ancillary ligand can be, for example, acetylacetonate or a phenylpyridine. The phenylpyridine can include one or more substituents. A substituent can be, for example, a halogen atom, such as a fluorine atom.

Figure 1:
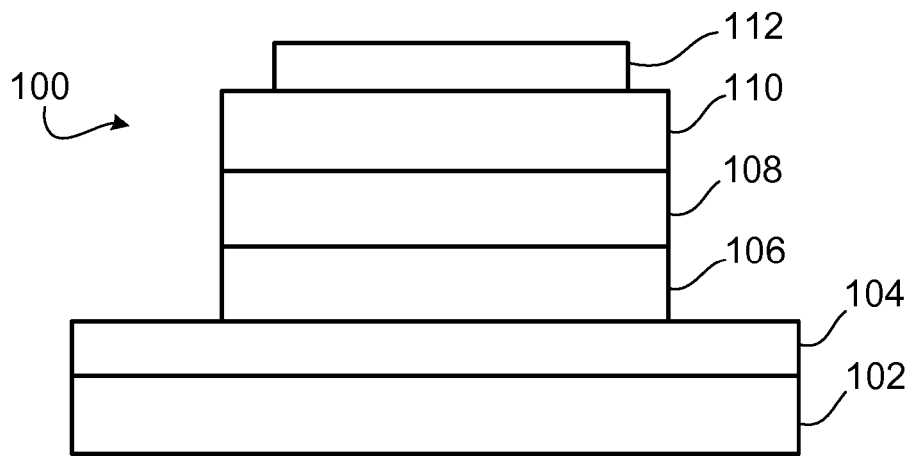
FIG. 1 is a schematic diagram of an organic light emitting device.
Figure 2:
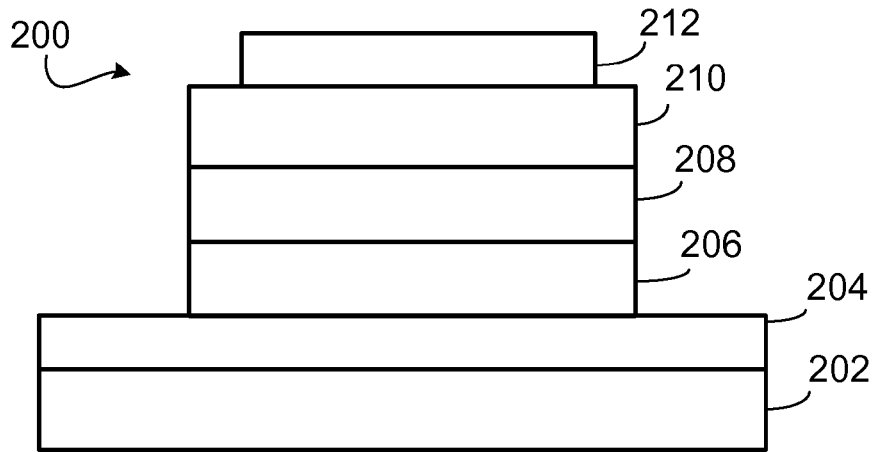
FIG. 2 is a schematic diagram of an organic solar cell.
Figure 3:
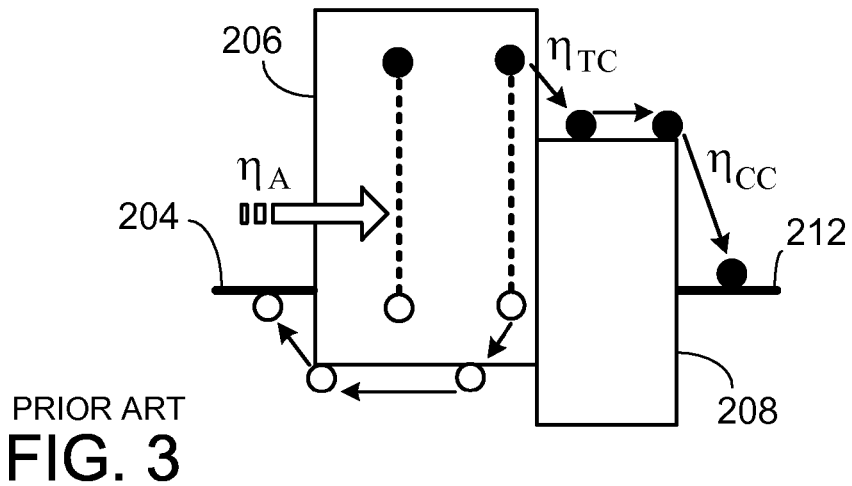
FIG. 3 illustrates schematically the process of generation of photocurrent from incident light in a donor-acceptor heterojunction photovoltaic cell.
Figure 4:
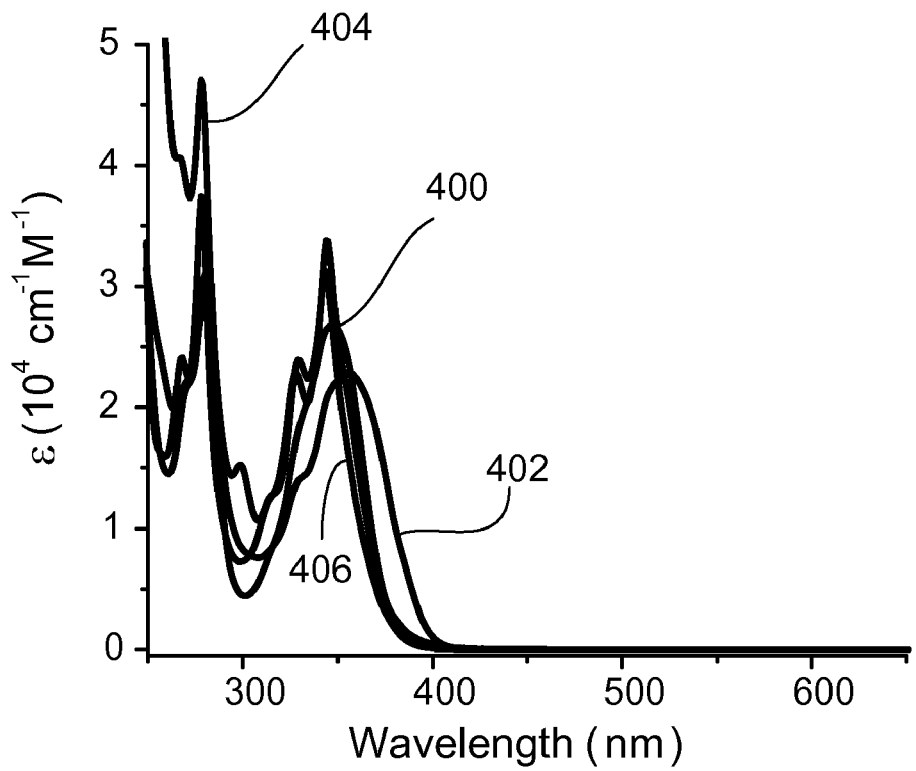
FIG. 4 shows absorbance spectra for free ligands with fused aromatic ring structures.

Free ligands described herein may have similar absorption spectra. For example, FIG. 4 shows absorbance spectra for pypy 400, pyq 402, pybq 404, and pyiq 406. These cyclometalating ligands bond with a transition metal to form organometallic complexes with a first bond between the transition metal and a nitrogen atom in an aromatic ring of the ligand and a second bond between the transition metal and a carbon atom in the fused aromatic ring structure of the ligand. When these ligands are bonded to Ir(III) with acetylacetonate (acac)

as an ancillary ligand, (C^N)₂Ir(acac) complexes with the following general structure are formed

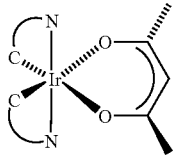

where —C^N— refers to:

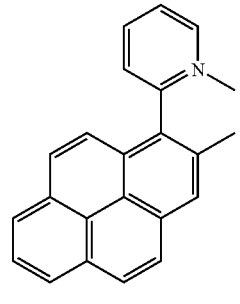
-pypy-

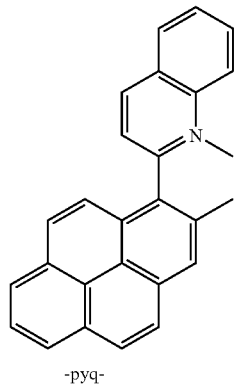
-pyq-

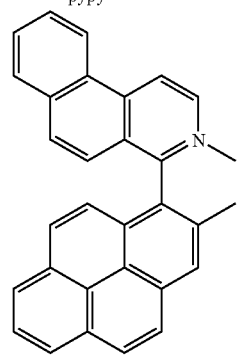
-pybq-

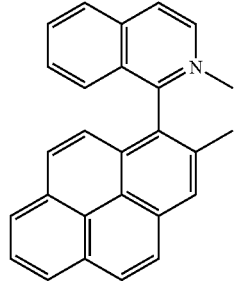
-pyiq-

Figure 5A:
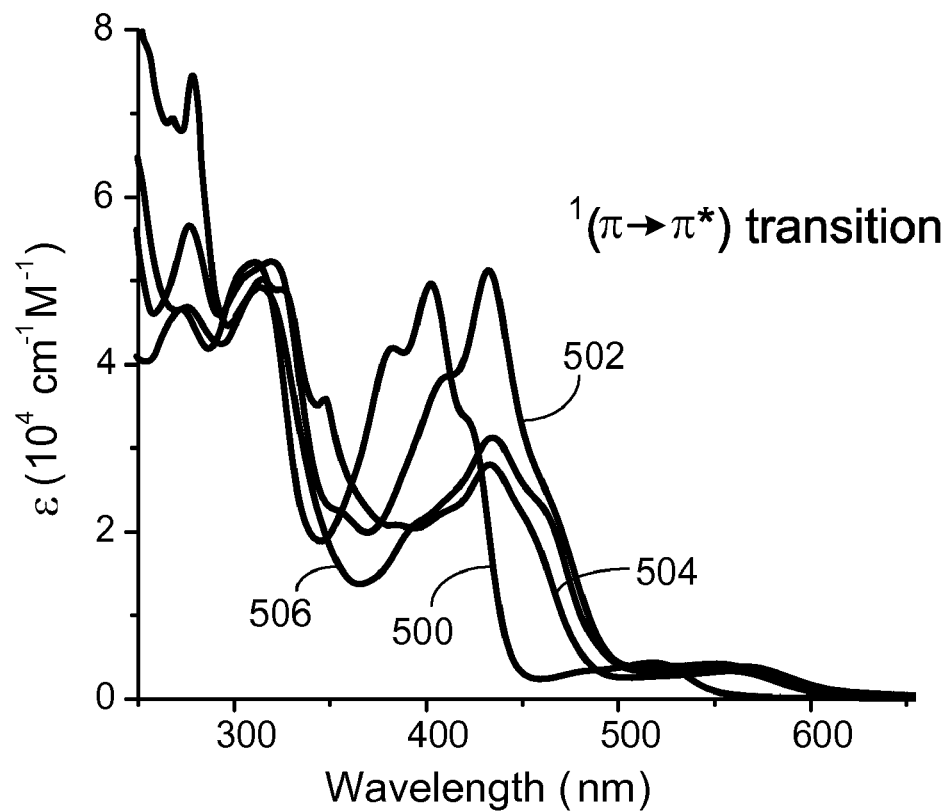
FIGS. 5A-C show absorbance spectra for various transitions in cyclometalated iridium complexes.
Figure 5B:
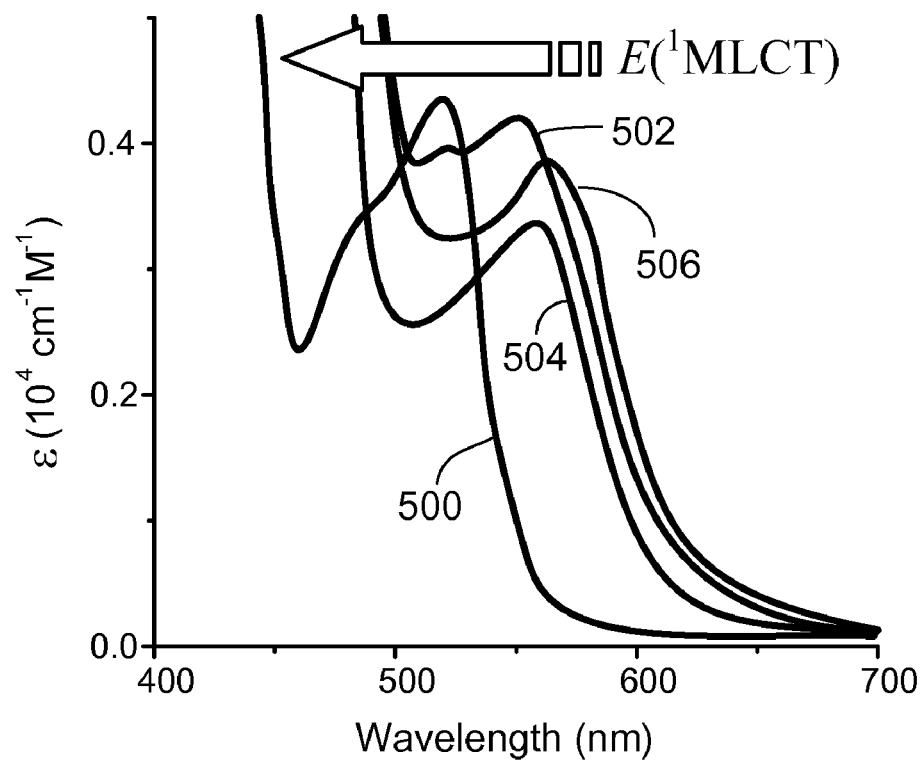
Figure 5C:
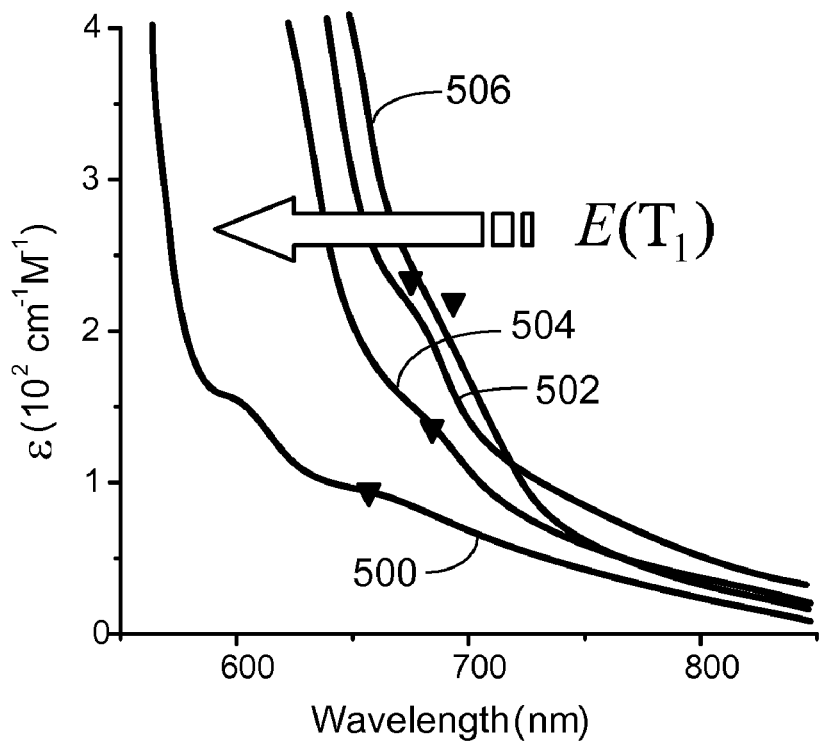
Figure 6:
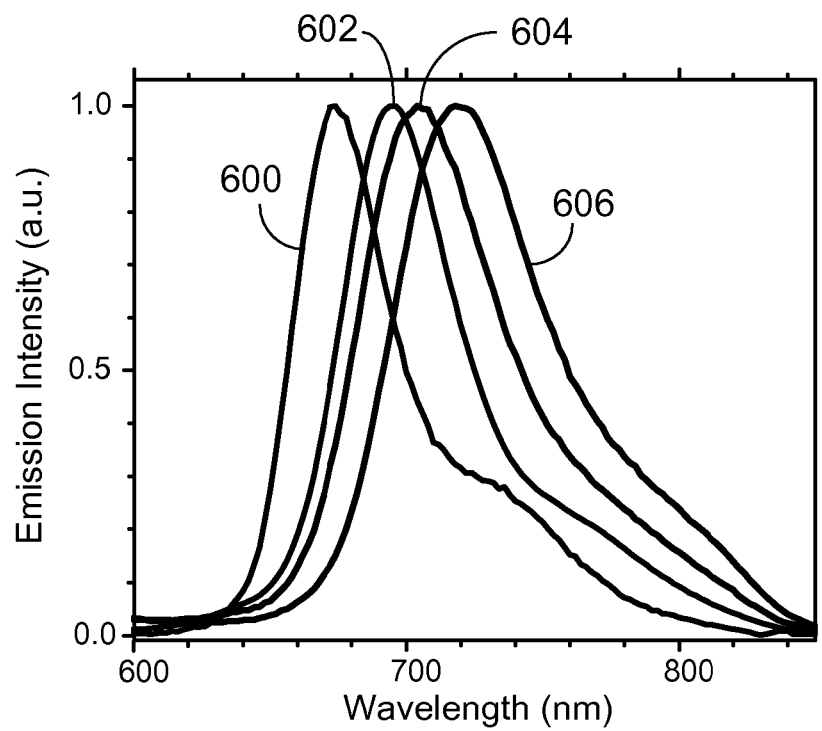
FIG. 6 slows emission spectra for cyclometalated iridium complexes.

As shown in FIGS. 5A-C, absorbance spectra of (pypy)₂Ir (acac) 500, (pyq)₂Ir(acac) 502, (pyba)₂Ir(acac) 504, and (pyiq)₂Ir(acac) 506 indicate shifting, or color tuning of the absorbance, as a function of the electron accepting portion of the cyclometalating ligand bonded to the pyrenyl group. FIG. 6 depicts color tuning, or a shift to longer emission wavelengths in the near infrared region from about 675 nm for (pypy)₂Ir(acac) 600, to about 695 nm for (pyq)₂IR(acac) 602, about 705 nm for (pyba)₂Ir(acac) 604, and about 720 nm for (pyiq)₂Ir(acac) 606. Thus, the wavelength of phosphorescent emission of the near infrared organometallic complex can be tuned by selecting the appropriate cyclometalating ligand.

Figure 7A:
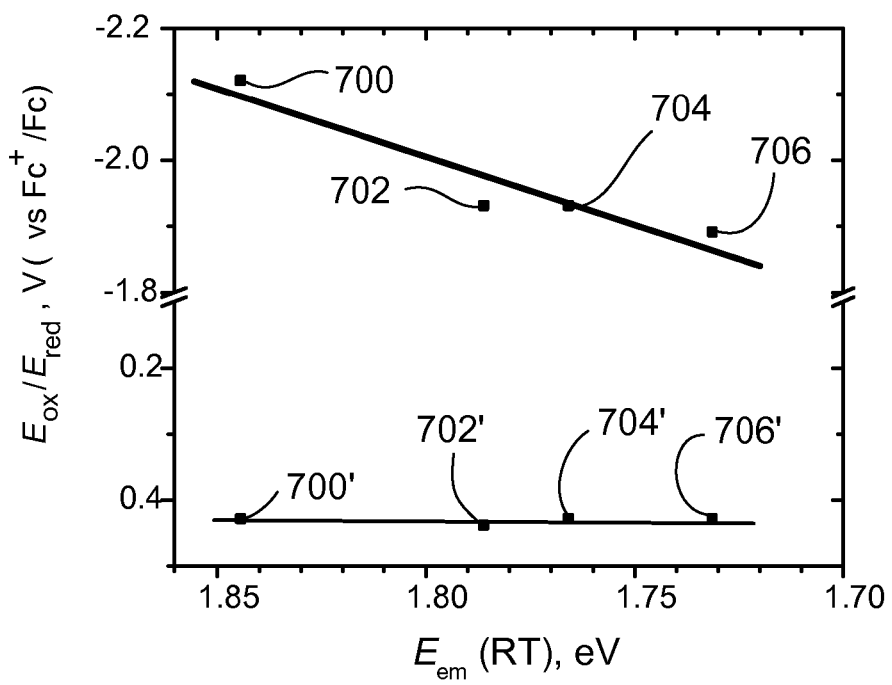
FIG. 7A shows plots of $E_{ox}$ and $E_{red}$ vs. $E_{em}$ for cyclometalated iridium complexes.
Figure 7B:
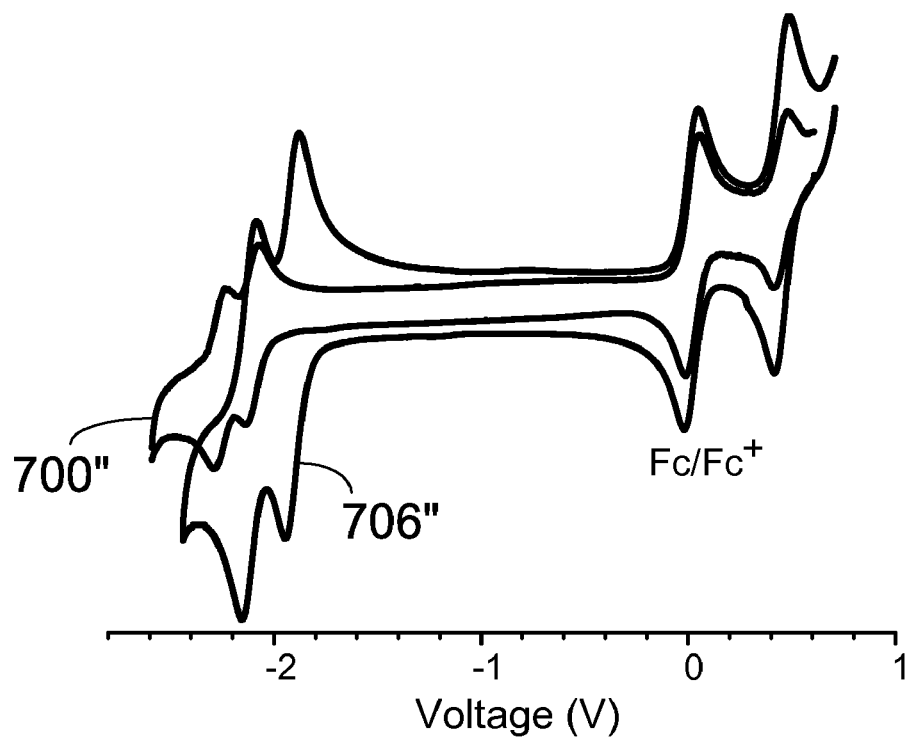
FIG. 7B shows cyclic voltammograms for two cyclometalated iridium complexes in FIG. 7A.

Without being bound by theory, it is believed that modification of the electron-accepting portion of the C^N ligands tunes the emission energy by lowering the lowest unoccupied molecular orbital (LUMO) level and leaving the highest occupied molecular orbital (HOMO) level substantially unchanged. This is supported by the plots in FIG. 7A, which show $E_{ox}$ and $E_{red}$ (vs. Fc⁺/Fc) vs. emission energy $E_{em}$(RT) for (pypy)₂Ir(acac) 700, 700', (pyq)₂IR(acac) 702, 702', (pyba)₂Ir(acac) 704, 704', and (pyiq)₂Ir(acac) 706, 706'. FIG. 7B shows cyclic voltammograms of (pypy)₂Ir(acac) 700" and (pyiq)₂Ir(acac) 706", which correspond to points 700' and 706' in FIG. 7A.

Other infrared phosphorescent organometallic complexes have the general structure

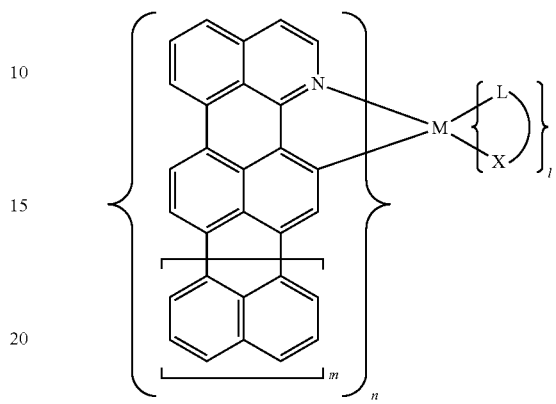

where M is Pt(II), Pd(II), Ir(III), or Rh(III), L^X is an ancillary ligand, n is an integer from 1 to 3, 1 is an integer from 0 to 2, and m is an integer $\geq 0$. When m=0, n=2, 1=1, and L^X is acetylacetonate, for example, the resulting organometallic complex is (azaperylene)₂Ir(acac).

Figure 8:
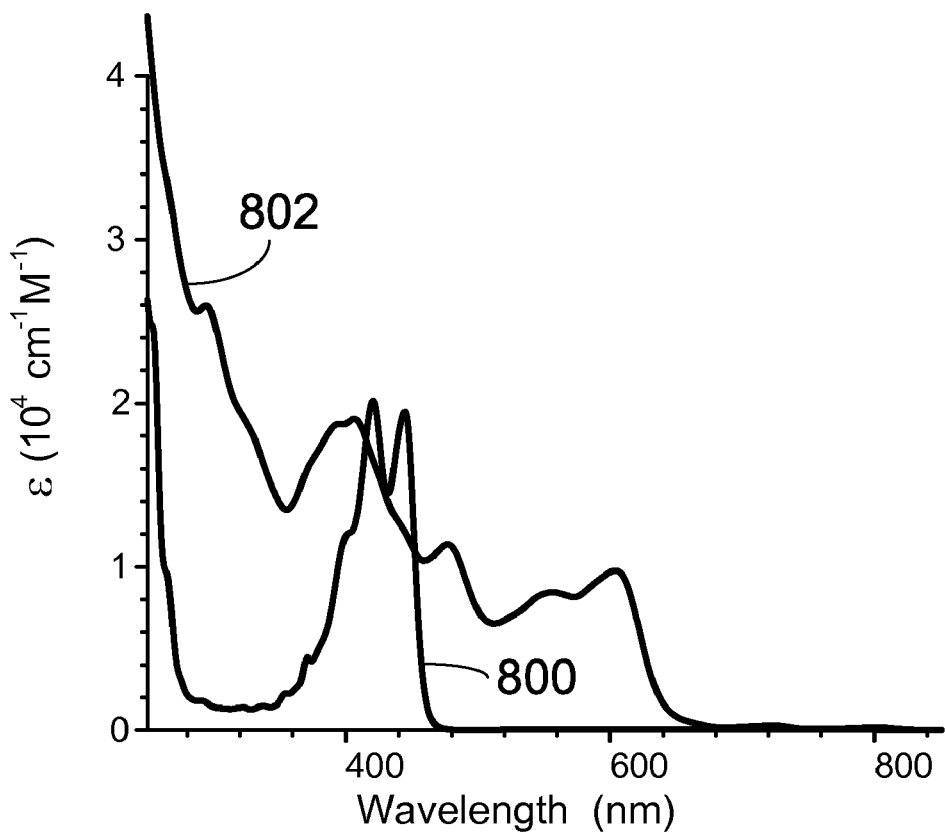
FIG. 8 shows absorption spectra of a free ligand and an organometallic complex including the same ligand.

FIG. 8 shows absorption spectra of azaperylene 800 and (azaperylene)₂Ir(acac) 802. The organometallic complex is expected to have a large exciton diffusion length due to its long exciton lifetime, due in part to the heavy metal and the interaction between the azaperylene and the metal. As seen in FIG. 8, compared with its organic counterpart, the organometallic complex has an extended absorption spectrum, which is desirable for better utilization of solar light in, for example, solar cells.

Figure 9:
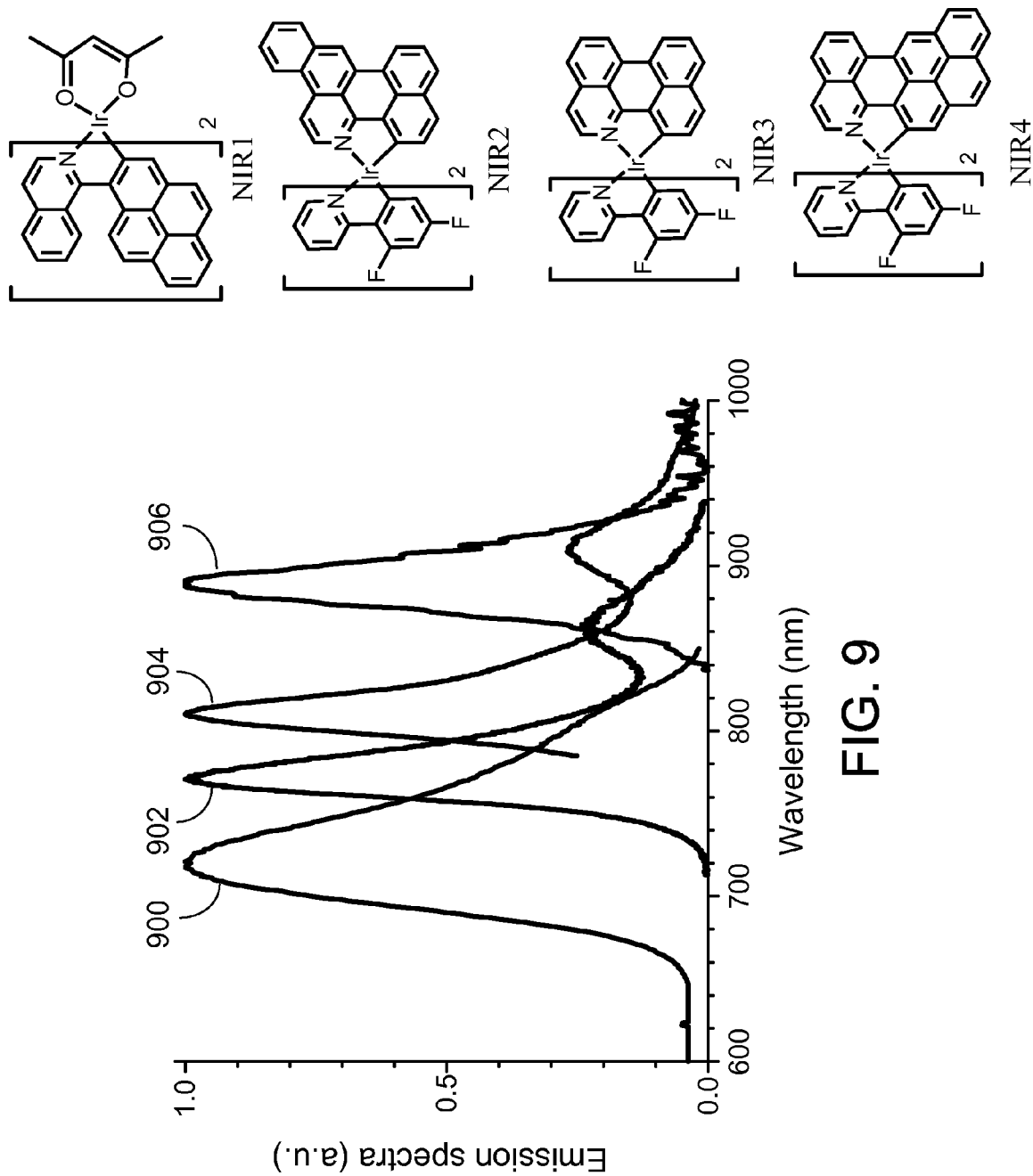
FIG. 9 shows the emission spectra and chemical structure of near infrared phosphorescent complexes.

FIG. 9 shows photoluminescence (emission) spectra of (pyiq)₂Ir(acac) (NIR1) 900 as well as other near infrared phosphorescent organometallic complexes NIR2, NIR3, and NIR4 (902, 904, and 906, respectively) with one aza-oligoryne cyclometalating ligand and two fluorine substituted phenylpyridine ancillary ligands. As seen in FIG. 9, the emission occurs over a range between about 650 nm and about 1000 nm. Wavelengths corresponding to the maximum intensity of the emission spectra of the aza-oligoryne organometallic complexes increase from about 780 nm for NIR2, to 820 nm for NIR3, to 900 nm for NIR4, while the maximum intensity of the emission spectrum for NIR1 is about 720 nm.

Figure 10:
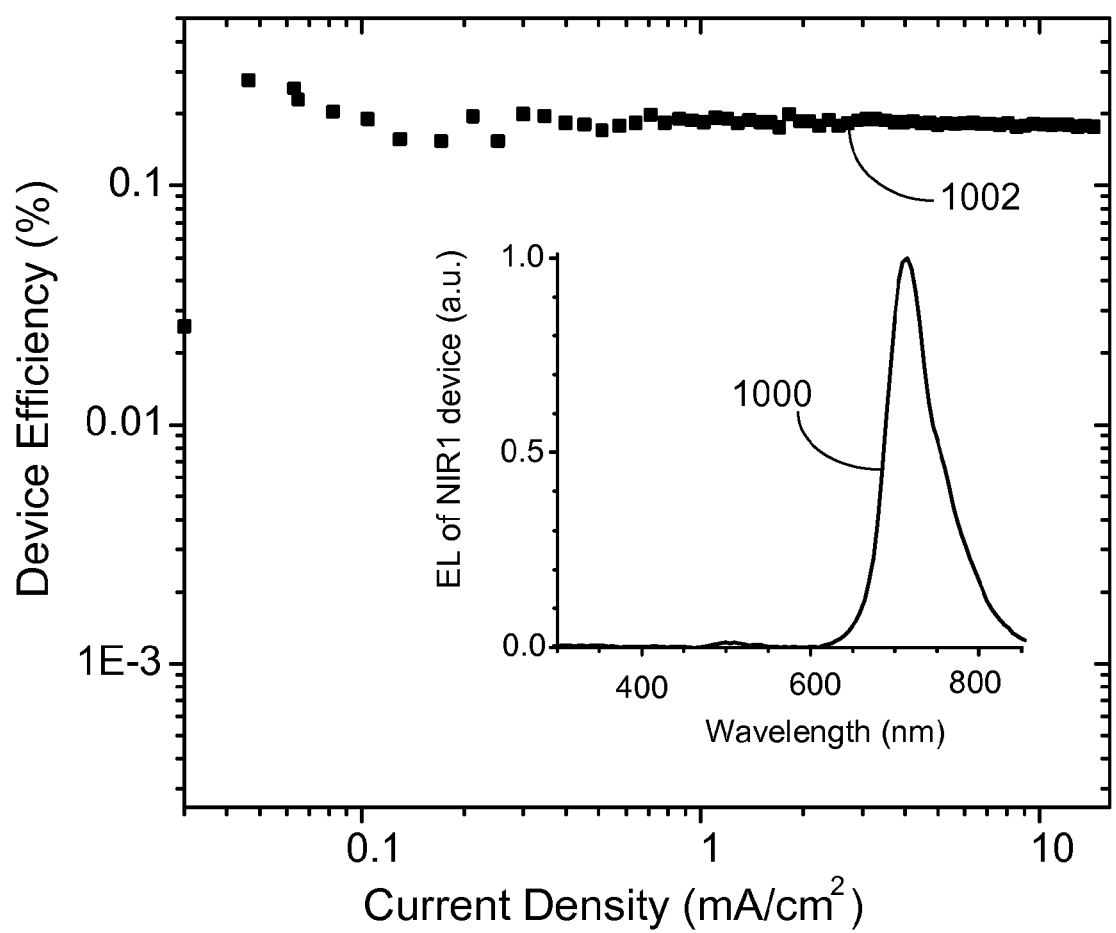
FIG. 10 shows device efficiency and an electroluminescent spectrum of OLED with a near infrared phosphorescent emitter.

FIG. 10 shows a near infrared electroluminescence spectrum 1000 from a device (ITO/PVK:PBD(30%):NIR1(20%)/BCP/Alq3/LiF/Al) with NIR1 as the emitter. Plot 1002 shows the device efficiency vs. current density (mA/cm²) for this device.

Figure 11A:
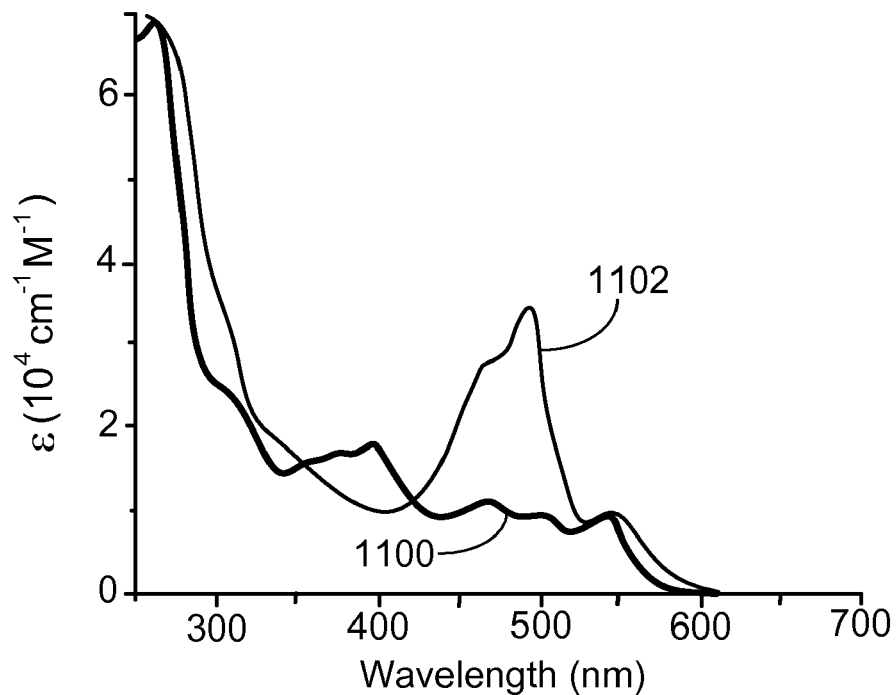
FIG. 11A shows absorbance spectra of two cyclometalated iridium complexes.
Figure 11B:
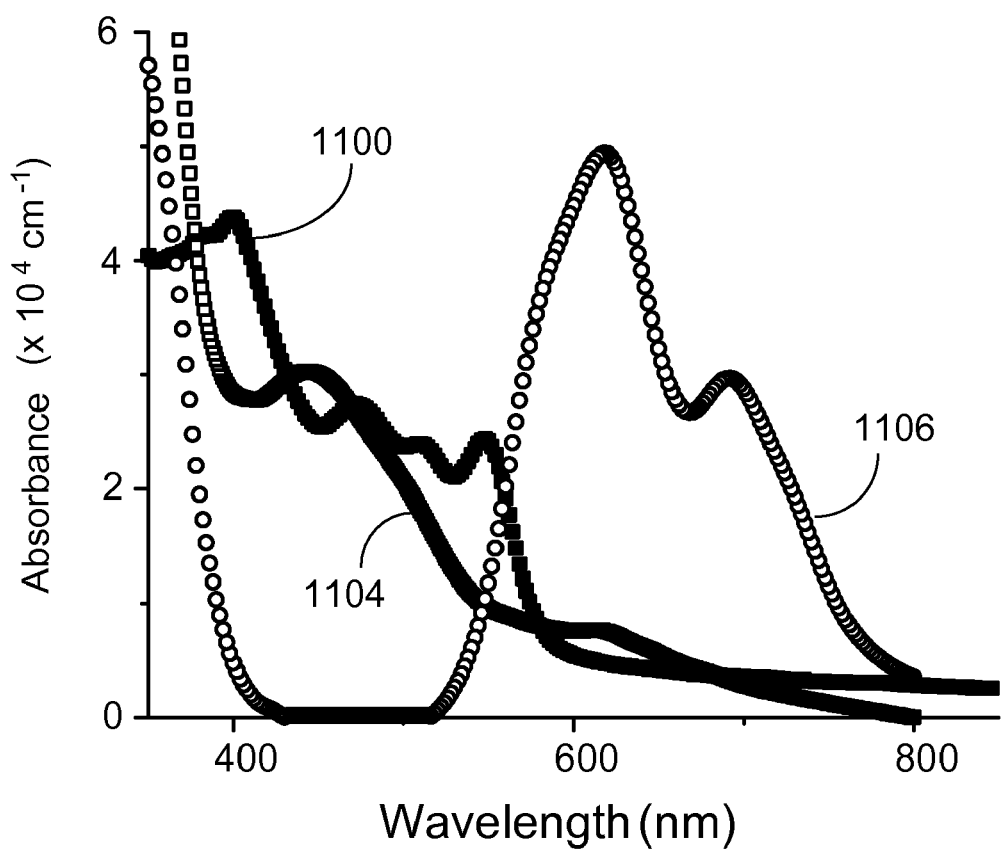
FIG. 11B shows absorbance spectra of a cyclometalated iridium complex and other absorbers for comparison.

FIG. 11A depicts absorption spectra for NIR3 1100 and NIR4 1102. As seen in FIG. 11A, these organometallic complexes have wide and intense absorption in the visible region. For comparison, FIG. 11B shows absorption spectra of NIR3 1100, C₆₀ 1104, and copper phthalocyanine (CuPc) 1106.

Figure 12A:
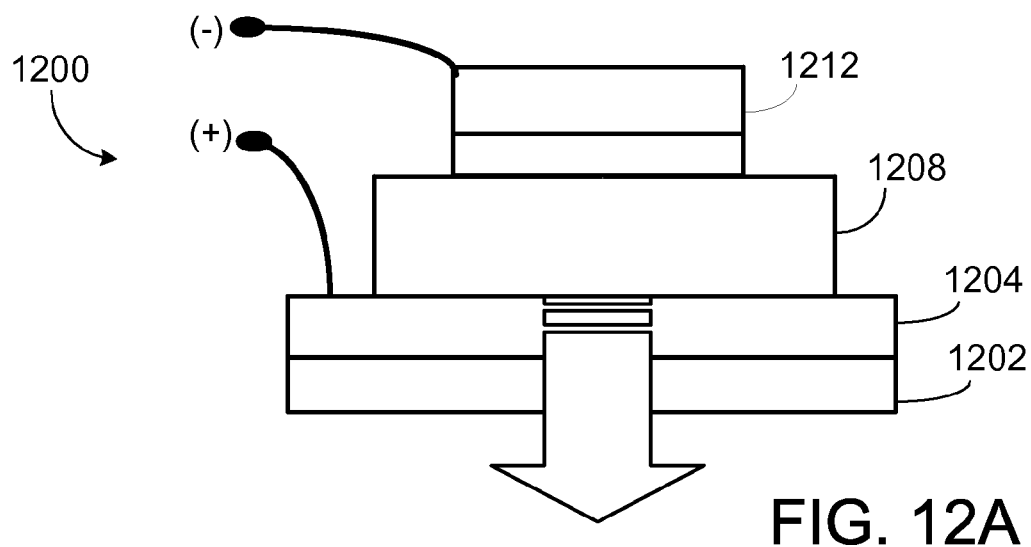
FIG. 12A is a schematic diagram of an OLED with a near infrared phosphorescent emitter.
Figure 12B:
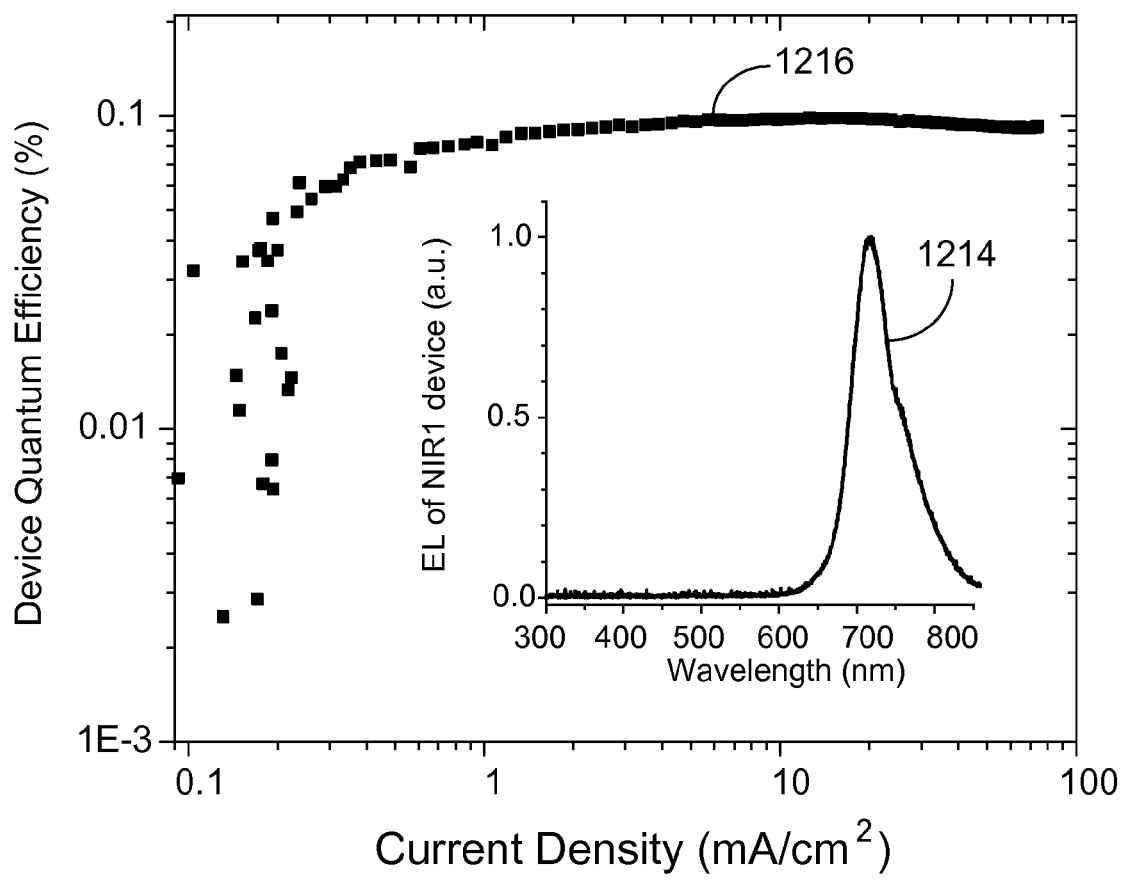
FIG. 12B shows the electroluminescence spectrum and the device efficiency for the OLED shown in FIG. 12A.

Spectral properties of the near infrared phosphorescent complexes described herein make these complexes particularly suitable for use as emitters and absorbers in OLEDs and organic solar cells. FIG. 12A shows an OLED 1200 with near infrared phosphorescent compound NIR1 as the emitter 1208. OLED 1200 includes substrate 1202, anode 1204, emitter layer 1208, and cathode 1212 (ITO/PVK:PBD(30%):

NIR1(20%)/BCP/Alq3/LiF/Al). FIG. 12B shows electroluminescence spectrum 1214 from OLED 1200, which demonstrates substantially exclusive near infrared emission. Plot 1216 shows a device efficiency of about 0.1% for OLED 1200. Maximum light output for OLED 1200 is about 0.12 mW/cm$^2$.

Figure 13A:
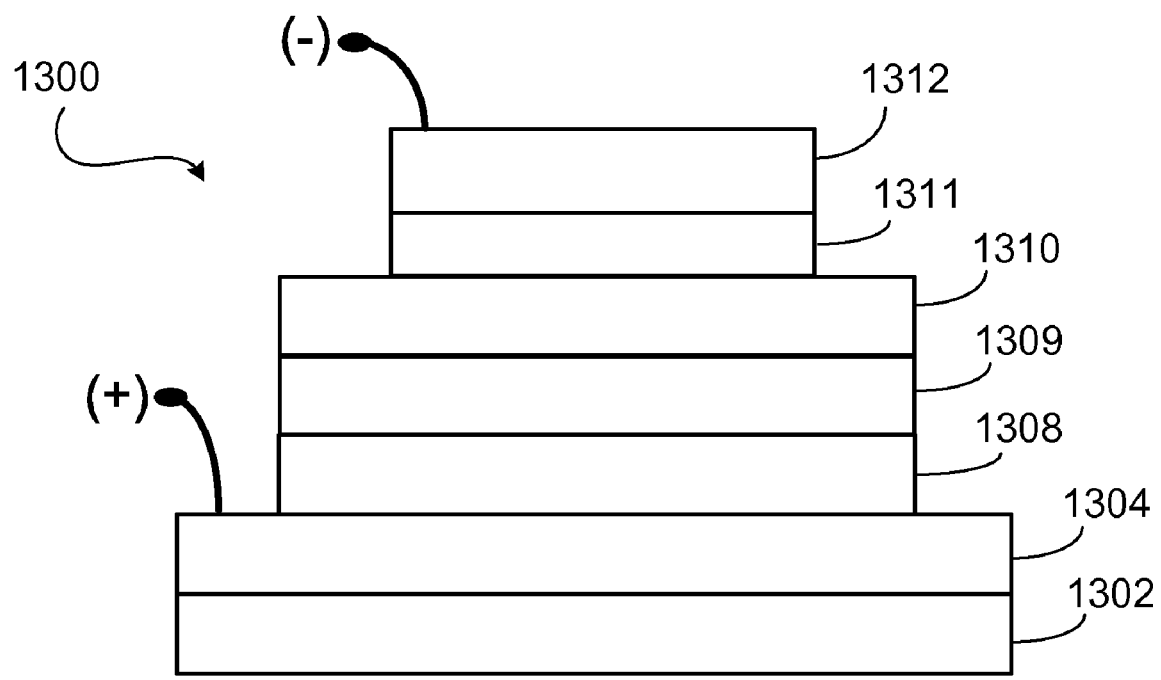
FIG. 13A is a schematic diagram of an OLED with a near infrared phosphorescent emitter.
Figure 13B:
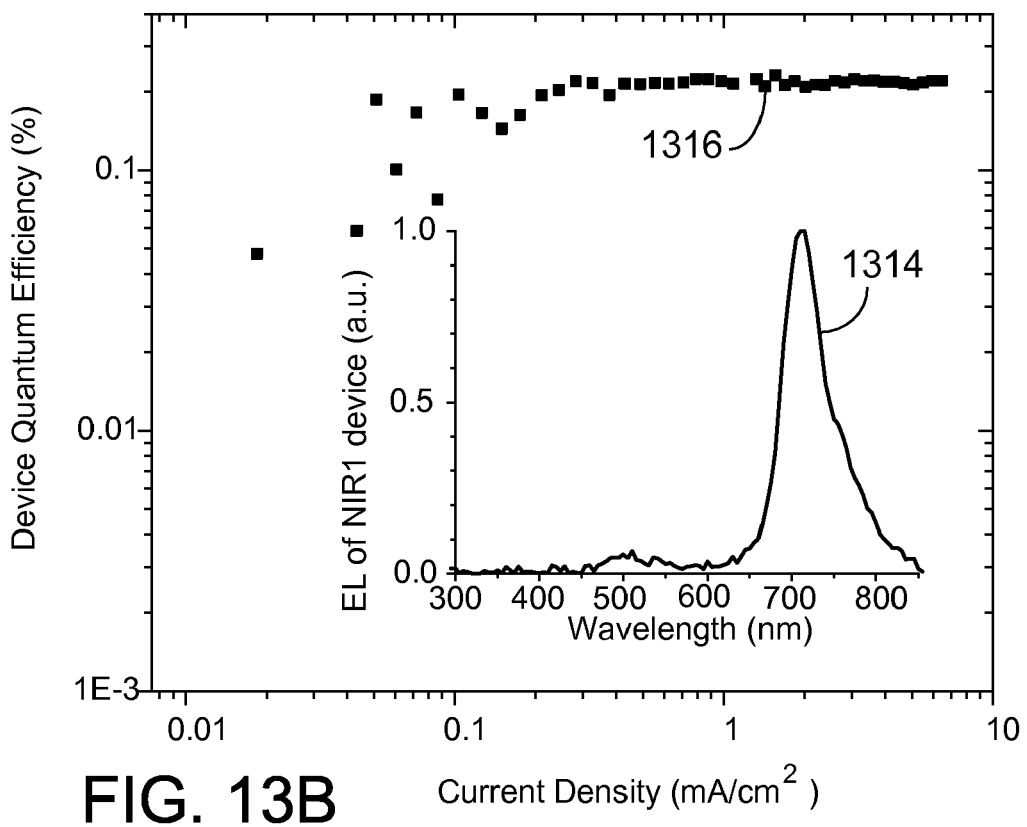
FIG. 13B shows the electroluminescence spectrum and the device efficiency for the OLED shown in FIG. 13A.
Figure 13C:
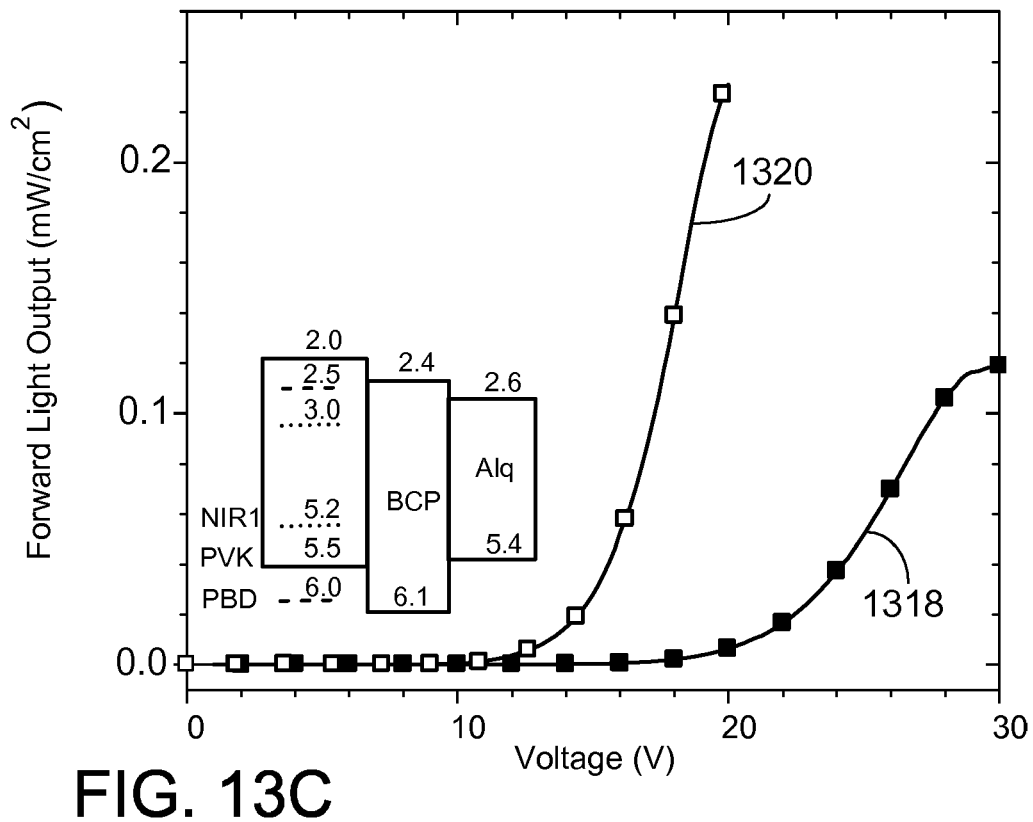
FIG. 13C shows the forward light output for the device shown in FIG. 13A, with and without BCP/Alq$_3$.

FIG. 13A shows an OLED 1300 with near infrared phosphorescent compound NIR1 as the emitter. OLED 1300 includes substrate 1302, anode 1304, emitter layer 1308, including NIR1 doped in a polymer host compound, BCP layer 1309, Alq3 layer 1310, LiF layer 1311, and aluminum cathode 1312. FIG. 13B shows electroluminescence spectrum 1314 from OLED 1300, which demonstrates a small portion of visible light together with the more intense near infrared emission. Plot 1316 shows a device efficiency of about 0.25% for OLED 1300. FIG. 13C shows the forward light output for OLED 1300 without BCP/Alq$_3$ 1318 and with BCP/Alq$_3$ 1320.

Figure 14:
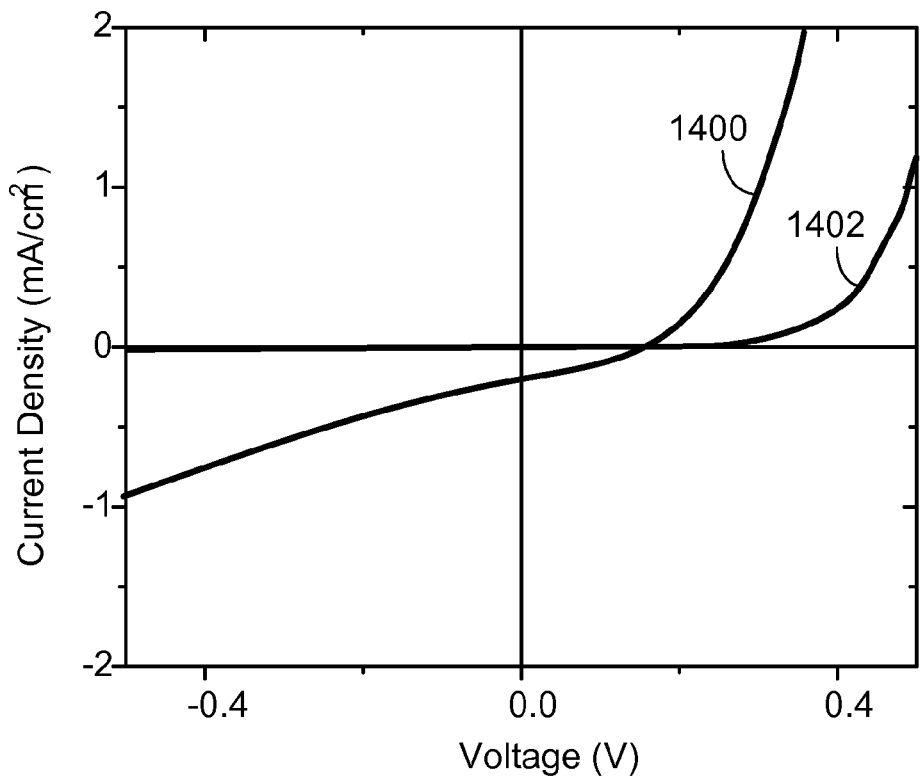
FIG. 14 is a plot of current density vs. voltage for an OLED in the presence and absence of sunlight.

FIG. 14 shows plots of current density vs. voltage for an OLED (ITO/PEDOT/NIR3:C60(34 nm)/C60(10 nm)/BCP (7.5 nm)/Ag in the presence of sunlight 1400 and in the absence of sunlight 1402.

EXAMPLE

Commercially available indium tin oxide (ITO) with sheet resistivity of 20Ω/☐ was used in the device fabrication process. Two device architectures were utilized to optimize energy transfer to and emission from NIR1. A 50 nm thick layer of poly(3, 4-ethylenedioxythiophene) poly(styrenesulfonate) (PEDOT:PSS) (CH8000, H. C. Stark) was spun on top of the ITO and dried at 190° C. for 10 min. The active layer was a blend of PVK (Aldrich), 2-(4-biphenyl)-5-(4-tert-butyl-phenyl)-1,3, 4oxadiazole (PDB) (Aldrich), and NIR1, dissolved in chloroform (Aldrich). PBD constituted 30% of the solute's total weight, and the NIR1 concentration was varied between 5% and 20% of the total weight. A bilayer LiF (1 nm)/Al(100 nm) structure was used as the cathode. The type I device used a 110 nm thick layer of the blend. The type II device was composed of a 60 nm blended layer followed by a 20 nm thick hole blocking layer of 2, 9-dimethyl-4,7-diphenyl-1,10-phenanthroline (BCP) (Aldrich) and a 20 nm thick electron injecting layer, tri(8-hydroxyquinoline)aluminum (Alq). The active area was 0.12 cm$^2$. The spin coating processes were carried out in ambient atmosphere while the BCP, Alq, LiF, and Al were vapor deposited at ($10^{-6}$ Torr) in a nitrogen glovebox contained vacuum chamber. The deposition rates were 0.8, 0.8, 0.06, and 2 Å/s, respectively.

Device characterization was carried out inside a nitrogen glovebox. Optical absorption photoluminescence (PL), and electroluminescence (EL) were measured using a Cary 5000 spectrophotometer. HORIBA Jobin Yvon Fluorolog-3, and Ocean Optics S2000 spectrometer. Current-voltage data were taken with a Keithley 2400 SourceMeter and optical power was measured using a Newport 2832-C power meter coupled to a calibrated Newport 818-UV/CM detector with a spectral response range from 190 to 1100 nm.

Figure 15:
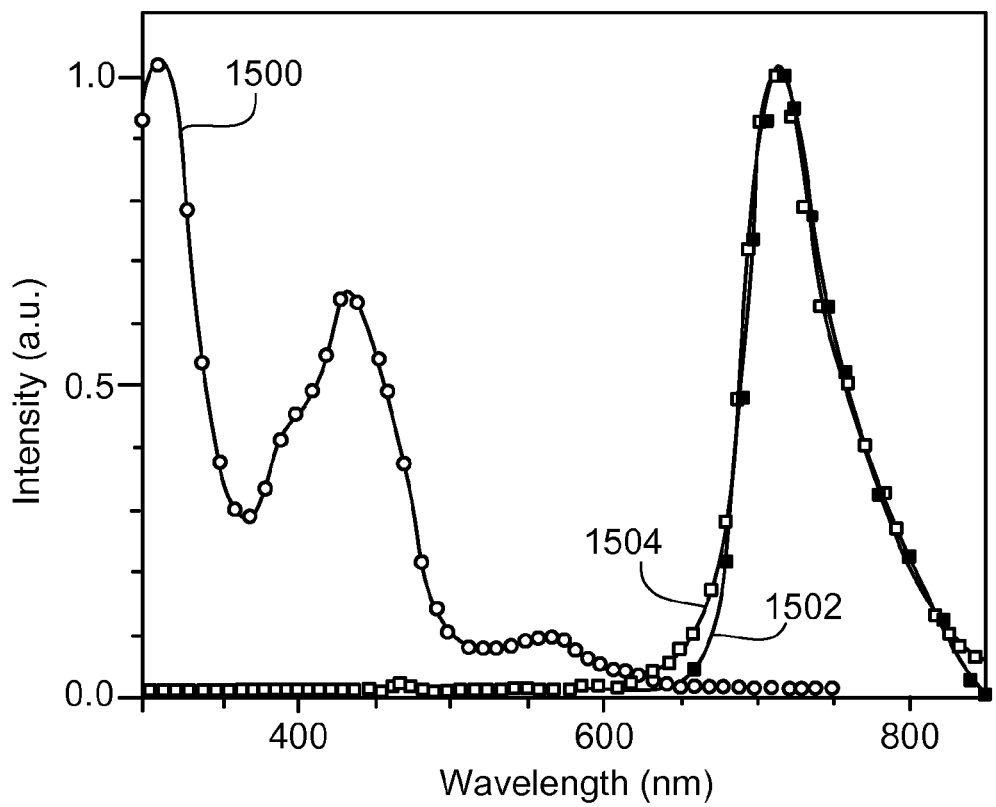
FIG. 15 shows absorbance and photoluminescence spectra of a near infrared phosphorescent organometallic complex and an electroluminescence spectrum of an OLED with the complex as the emitter.

FIG. 15 shows the absorbance spectrum 1500, the photoluminescence spectrum 1502, and the electroluminescence spectrum 1504 of single-layer, type I devices. Electroluminescence spectra show substantially exclusive near infrared emission from NIR1 for all investigated doping concentrations.

Table I shows device characteristics for type I (ITO/PEDOT/PVK:PBD:NIR1/LiF/Al) and type II (ITO/PEDOT/PVK:PBD:NIR1/Alq/LiF/Al) devices. External quantum efficiency $\eta_{ext}$ and operational voltage are given as functions of current density (J). Maximum forward light output (FLO) and fraction of total emission attributed to near infrared emission, at peak quantum efficiency, are listed. Table I reveals a trend of decreasing voltage, for specified current, with increasing NIR1 doping concentration.

TABLE I

Characteristics of phosphorescent devices.

| NIR 1 conc. | Device | $\eta_{ext}$ (%) at J (mA/cm$^2$) | | | Voltage (V) at J (mA/cm$^2$) | | | Max FLO | % of power in |
|---|---|---|---|---|---|---|---|---|---|
| (%) | type | J = 1 | J = 10 | J = 50 | J = 1 | J = 10 | J = 50 | (mW/cm$^2$) | NIR |
| 5 | I | 0.082 | 0.097 | 0.092 | 17.4 | 22.0 | 26.6 | 0.119 | 100 |
| 10 | I | 0.073 | 0.085 | 0.080 | 16.0 | 20.8 | 25.8 | 0.105 | 100 |
| 15 | I | 0.016 | 0.075 | 0.075 | 13.4 | 17.2 | 21.6 | 0.122 | 100 |
| 20 | I | 0.037 | 0.050 | 0.058 | 12.6 | 16.2 | 20.0 | 0.112 | 100 |
| 5 | II | 0.266 | 0.245 | 0.213 | 12.4 | 15.8 | 19.2 | 0.238 | 77 |
| 10 | II | 0.210 | 0.213 | 0.193 | 11.8 | 15.6 | 18.8 | 0.319 | 88 |
| 15 | II | 0.184 | 0.191 | 0.178 | 10.4 | 14.2 | 17.2 | 0.290 | 92 |
| 20 | II | 0.156 | 0.162 | 0.153 | 9.2 | 12.8 | 15.6 | 0.290 | 93 |

Figure 16A:
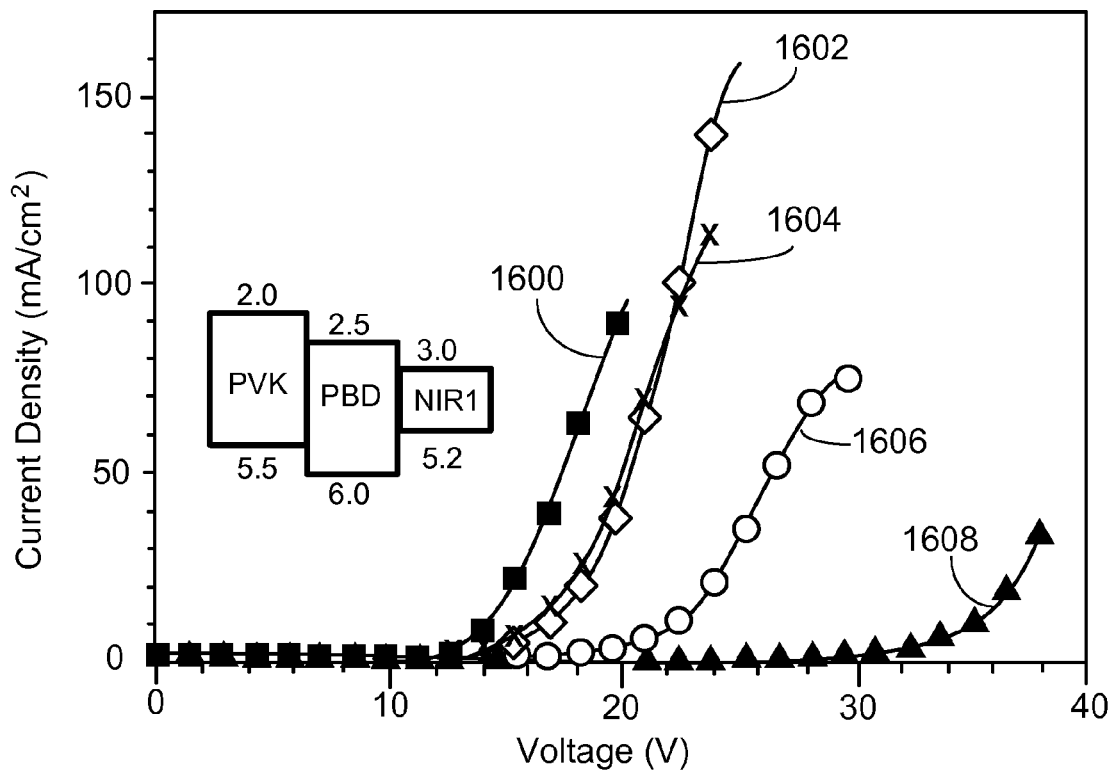
FIG. 16A shows current density vs. voltage for OLEDs of varying dopant/host concentrations.
Figure 16B:
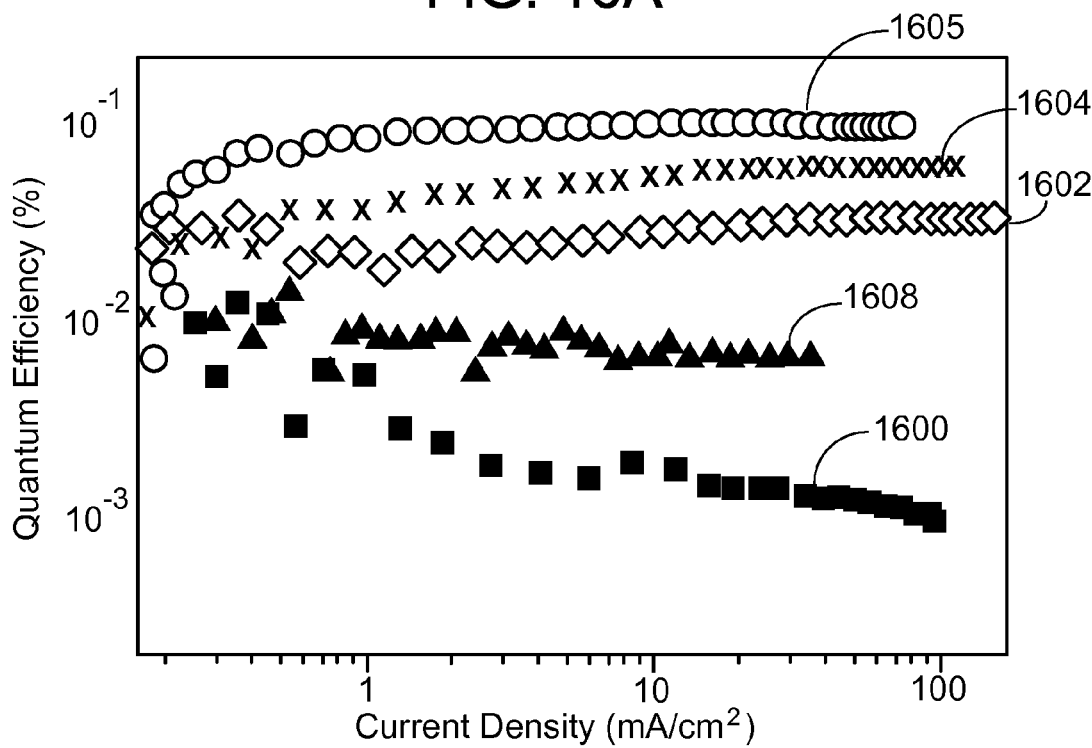
FIG. 16B shows quantum efficiency for the OLEDs in FIG. 16A.

FIG. 16A shows current density vs. voltage for a control device with a neat PVK film 1600, NIR1(20%):PVK 1602, NIR1(20%):PBD(30%):PVK 1604, NIR1(5%):PBD(30%):PVK 1606, and NIR1(5%):PVK 1608. The neat PVK film displays the lowest operational voltage. The higher operational voltage in devices having PVK:NIR1 (5%) suggests a hole-trapping process due to the higher HOMO of NIR1. With increasing NIR1 concentration, as is the case with devices utilizing PVK:NIR1 (20%), the distance between the dopant sites decreases; this further facilitates charge hopping and leads to the lower operational voltage. Upon the addition of PBD, a known electron transport material, a lower operational voltage is observed in PVK:PBD:NIR1 (5%), as compared to PVK:NIR1(5%). When the concentration of NIR1 increases to 20%, the presence of PBD does not appear to affect the current-voltage characteristics of the device, but does show a marked improvement in quantum efficiency, as shown in FIG. 16B, for PVK film 1600, NIR1(5%):PVK 1608, NIR1(20%):PVK 1602, NIR1(20%):PBD(30%):PVK 1604, and NIR1(5%):PBD(30%):PVK 1606.

The enhancement in quantum efficiency for devices incorporating PBD can be attributed to improved electron transport, which allows electrons to travel further in the device, extending the recombination zone and reducing the effect of quenching by the cathode. This increased transport also allows for more direct charge trapping by NIR1, as its HOMO and LUMO levels lie within the band gap of PBD and PVK. Moreover, there is strong overlap of both PVK and PBD emissions with NIR1 absorption spectra.

Although the PBC content is the same for PVK:PBD:NIR1 (5%) and PVK:PBD:NIR1(20%), a higher quantum efficiency can be seen for 5% doping (FIG. 15B). The decrease with increasing doping may be due to quenching effects arising from aggregation of the phosphorescent dye.

Figure 17:
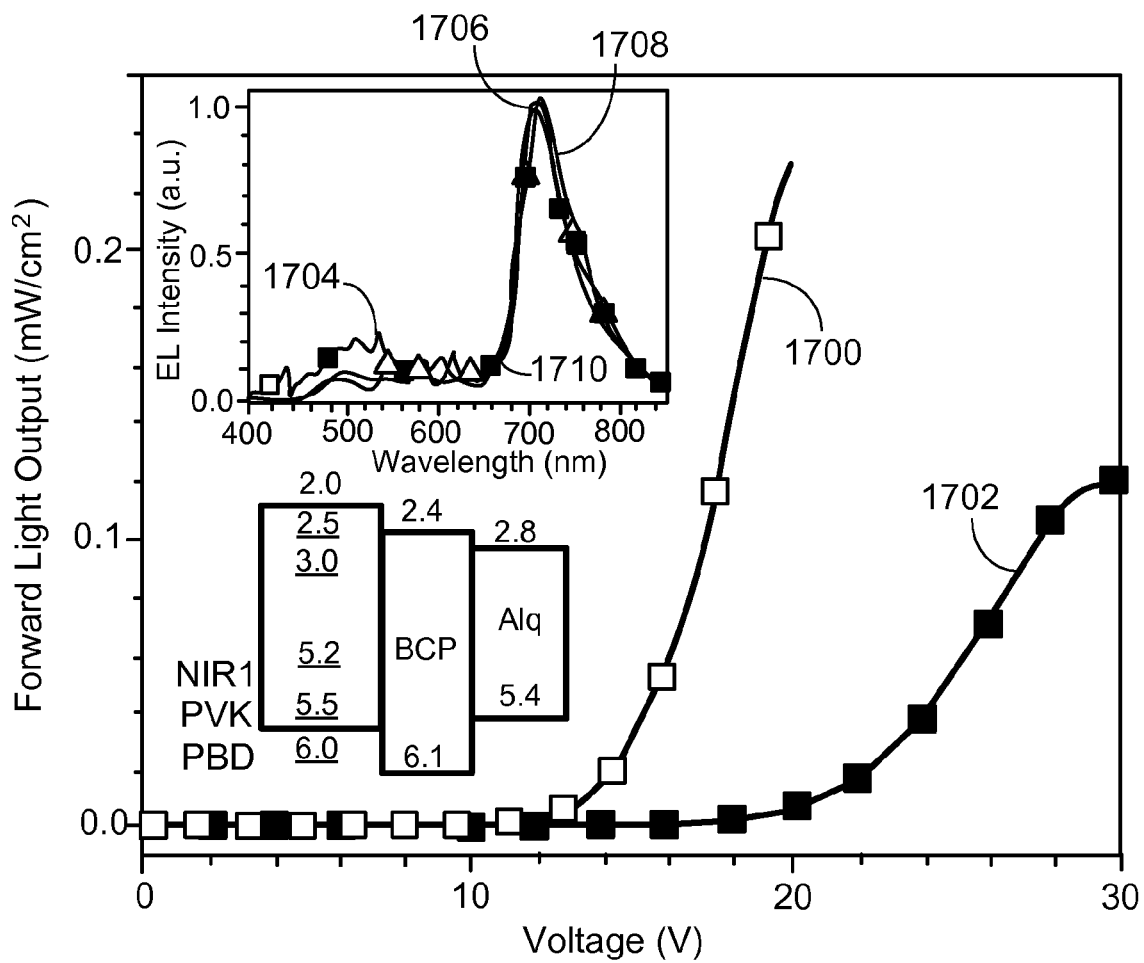
FIG. 17 shows forward light output vs. bias voltage characteristics for phosphorescent OLEDs and electroluminescence spectra of the OLEDs.

It was expected that by incorporating a BCP layer (type II device), holes would be mostly prevented from traversing the device, thus positioning the recombination zone away from the cathode and allowing for more efficient emission from NIR1. FIG. 17 shows forward light output vs. bias voltage characteristics for ITO/PEDOT/PVK:PBD:NIR1(5%)/LiF/Al 1700 and ITO/PEDOT/PVK:PBD:NIR1(5%)/BCP/Alq$_3$/LiF/Al 1702. The inset shows electroluminescence spectra of devices with type II structure (ITO/PEDOT/PVK:PBD:NIR1/BCP/Alq$_3$/LiF/Al) with NIR1 concentrations of 5%, 10%, 15%, and 20% denoted as 1704, 1706, 1708, and 1710, respectively.

As seen in FIG. 17 and Table I, the operational voltage is decreased and the total light output and quantum efficiency are both enhanced. However, the devices exhibited additional emission around 430 to 600 nm (FIG. 16B). This additional emission accounts for, respectively, 23%, 12%, 8%, and 7% of the total emission for 5%, 10%, 15%, and 20% by weight NIR1 dopant concentrations for voltages at which peak quantum efficiency was obtained.

For type I and type II devices, at all doping concentrations, forward light output was ill excess of 100 μW/cm$^2$. NIR1 doping of 5% proved most efficient for both device types containing PBD.

This example shows exclusive near infrared emission with a peak wavelength of 720 nm from a rationally designed Ir-based heavy metal complex doped into a PVK:PBD matrix. The peak quantum efficiency was about 0.1%. Forward light output exceeded 100 μW/cm$^2$. Inclusion of hole blocking layers and electron injecting layers improved quantum efficiency to above 0.25%, with 77% of the total light attributed to NIR1.

A number of embodiments of the invention have been described. Nevertheless, it will be understood that various modifications may be made without departing from the spirit and scope of the invention. Accordingly, other embodiments are within the scope of the following claims.

What is claimed is:

1. An organometallic complex comprising:
   a cyclometalating ligand selected from the group consisting of pyrenyl-pyridine, pyrenyl-quinolone, pyrenyl-benziso-quinolone, and pyrenyl-iso-quinolone;
   an acetylacetonate ancillary ligand; and
   a transition metal bonded to the cyclometalating ligand and the acetylacetonate ancillary ligand,
   wherein the organometallic complex is capable of phosphorescent emission with maximum emission intensity occurring at a wavelength in a range from about 650 nm to about 2000 nm, and
   wherein the organometallic complex is not a pyrenyl-pyridine Ir(III) complex.

2. The complex of claim 1, wherein the transition metal is selected from the group consisting of Pt(II), Pd(II), Ir(III), and Rh(III).

3. The complex of claim 1, further comprising at least one additional cyclometalating ligand selected from the group consisting of pyrenyl-pyridine, pyrenyl-quinolone, pyrenyl-benziso-quinolone, and pyrenyl-iso-quinolone.

4. The complex of claim 1, wherein the wavelength of maximum emission intensity is tunable.

5. A phosphorescent organic light emitting device comprising the organometallic complex of claim 1.

6. A phosphorescent device, comprising:
   a phosphorescent emitter in a host material, wherein the phosphorescent emitter is the organometallic complex of claim 1 and
   wherein the fraction of total emission attributed to near infrared is at least about 75%.

7. The device of claim 6, wherein the fraction of total emission attributed to near infrared is at least about 90%.

8. The device of claim 6, wherein the phosphorescent device is an organic light emitting device.

9. The device of claim 6, wherein the phosphorescent device is an organic solar cell.

10. A night vision display device comprising the phosphorescent device of claim 6.

* * * * *